United States Patent [19]

D'Silva

[11] Patent Number: 4,595,769
[45] Date of Patent: Jun. 17, 1986

[54] CARBAMATE-SULFENYL-CARBAMOYL FLUORIDE COMPOUNDS

[75] Inventor: Themistocles D. J. D'Silva, South Charleston, W. Va.

[73] Assignee: Union Carbide Corporation, Danbury, Conn.

[21] Appl. No.: 602,255

[22] Filed: Apr. 20, 1984

Related U.S. Application Data

[63] Continuation of Ser. No. 192,601, Sep. 30, 1980, abandoned, which is a continuation of Ser. No. 737,219, Nov. 4, 1976, abandoned, which is a continuation-in-part of Ser. No. 636,629, Dec. 1, 1975, Pat. No. 4,338,450.

[51] Int. Cl.$^4$ ............... C07C 161/00; C07D 307/79; C07D 317/64; C07D 333/54
[52] U.S. Cl. ..................... 549/470; 260/402.5; 260/544 C; 549/39; 549/51; 549/438; 549/452; 560/9; 560/133; 560/134; 560/135; 560/136; 560/137; 560/148; 558/408; 558/415
[58] Field of Search ............... 560/134, 137, 9, 133, 560/135, 136, 148; 549/39, 56, 438, 451, 466, 51, 452, 462, 471, 470; 260/544 C, 465 D, 465.4, 402.5

[56] References Cited

U.S. PATENT DOCUMENTS

| | | | |
|---|---|---|---|
| 3,344,153 | 9/1967 | Kuhle et al. | 424/320 |
| 3,349,125 | 10/1967 | Ratz et al. | 564/39 |
| 3,557,190 | 1/1971 | Buchanan | 260/482 |
| 3,639,471 | 2/1972 | Klauke et al. | 260/544 C |
| 3,663,594 | 5/1972 | Brown et al. | 560/137 |
| 3,699,122 | 10/1972 | Kohn | 260/326.5 S |
| 3,699,163 | 10/1972 | Kohn | 260/544 C |
| 3,726,908 | 4/1973 | Buchanan | 260/453.8 |
| 3,781,331 | 12/1973 | Kuhle et al. | 560/137 |
| 3,928,407 | 12/1975 | Brown et al. | 71/98 |
| 3,939,192 | 2/1976 | Kuhle et al. | 260/453 |
| 4,338,450 | 7/1982 | D'Silva | 548/185 |

FOREIGN PATENT DOCUMENTS

| | | | |
|---|---|---|---|
| 717705 | 6/1969 | Belgium . | |
| 0772634 | 11/1970 | Belgium | 260/544 C |
| 772634 | 11/1970 | Belgium | 260/544 C |
| 1297095 | 6/1969 | Fed. Rep. of Germany . | |
| 1189915 | 4/1970 | United Kingdom . | |

*Primary Examiner*—Natalie Trousof
*Assistant Examiner*—Patricia M. Scott
*Attorney, Agent, or Firm*—Gerald L. Cooh; C. J. Vicari

[57] ABSTRACT

Carbamate-sulfenyl-carbamoyl fluoride compounds are valuable insecticidal compositions and are also useful intermediates in the production of bis-carbamate compounds.

18 Claims, No Drawings

CARBAMATE-SULFENYL-CARBAMOYL FLUORIDE COMPOUNDS

This is a continuation of our prior U.S. application Ser. No. 192,601, filed Sept. 30, 1980, now abandoned, which is a continuation of application Ser. No. 737,219, filed Nov. 4, 1976, now abandoned, which is a continuation-in-part of application Ser. No. 636,629, filed Dec. 1, 1975, now U.S. Pat. No. 4,338,450.

This invention relates to a novel class of carbamatesulfenyl-carbamoyl fluoride compounds and to their preparation.

The novel compounds of this invention are compounds corresponding to the following general formula:

$$\overset{O}{\underset{\|}{F C}}-\overset{R}{\underset{|}{N}}-S-\overset{R'}{\underset{|}{N}}-\overset{O}{\underset{\|}{C}}-R''$$

wherein:
R and R' are the same or different and are alkyl groups having from one to four carbon atoms;
R'' is:
(a) hydrogen; or
(b) alkyl, cycloalkyl, phenyl, phenylalkyl, naphthyl, alkenyloxy, alkynyloxy, phenoxy, 5,6,7,8-tetrahydronaphthoxy, naphthoxy, benzofuranoxy, benzothienoxy or methylenedioxyphenoxy all of which may be unsubstituted or substituted with one or more chloro, bromo, fluoro, cyano, nitro, alkyl, alkynyloxy, phenoxy, phenyl, 2-dithiolanyl, 2-dioxalanyl, alkoxy, haloalkyl, dialkylamino, cyanoalkyl dicyanoethylidene or alkylthio groups in any combination; or
(c) a group of the formula:

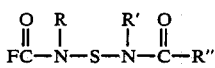

wherein:
R₁ is hydrogen, alkyl or alkylthio or cyano;
R₂ is alkyl, alkylthio, alkoxy, alkanoyl, alkoxycarbonyl, aminocarbonyl, alkylaminocarbonyl or dialkylainocarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl groups or R₂ is phenyl, aminocarbonyl, alkylaminocarbonyl, dialkylaminocarbonyl or an R₃CONH— or R₃CON(alkyl)group where R₃ is hydrogen, alkyl or alkoxy; and
A is a divalent aliphatic chain, completing a five or six member ring, which includes one or two divalent oxygen, sulfur, sulfinyl or sulfonyl groups and which may also include one divalent amino, alkylamino or carbonyl group; in any combination; provided that the total number of aliphatic carbon atoms in R₁, R₂ and A, individually, may not exceed eight.

Preferred compounds according to this invention are those wherein R and R' are both methyl.

Many of these compounds are themselves useful as insecticides, miticides, and nematocides. All of these compounds are useful as intermediates in the preparation of pesticidal compositions by reaction with oxime compounds of form bis-carbamate compounds joined by a sulfenyl radical. For example, 1-methylthioacetaldehyde O-[N-methyl-N-(N'-methyl-N'-fluoroformylaminosulfenyl)carbamoyl]oxime may be reacted with 2-methylthio-2-methylpropionaldoxime in the presence of an acid acceptor to yield N-[2-methylthio-2-methylpropionaldehyde O-(N-methylcarbamoyl)oxime]N-[1-methylthioacetaldehyde-O-(N'-methylcarbamoyl)oxime]sulfide, which exhibits outstanding insecticidal and miticidal properties. The preparation and utility of such bis-carbamate compounds, produced by reacting compounds according to this invention with oxime compositions and other active hydrogen containing compounds is more fully described in my copending U.S. patent application Ser. No. 636,630, filed Dec. 1, 1975; now abandoned, entitled "Unsymmetrical Bis-Carbamate Compounds."

Such unsymmetrical bis-carbamoyl sulfides can be prepared conveniently by the method shown in the following general reaction scheme:

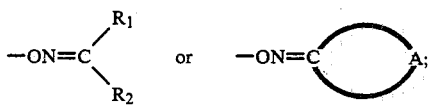

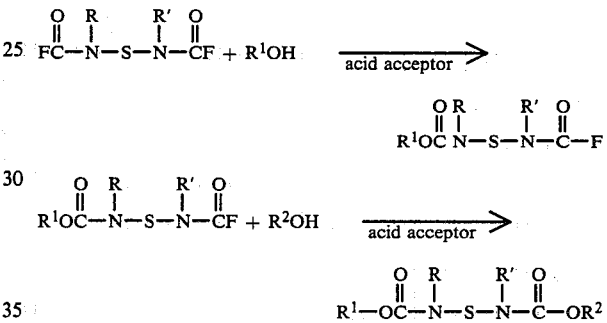

wherein:
R and R' are individually alkyl radicals having from 1 to 4 carbon atoms; R¹ is:

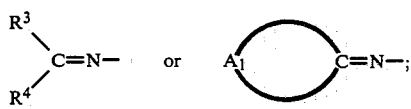

R² is other than R¹ and is alkenyl, alkynyl, phenyl, benzofuranyl, benzothienyl, naphthyl or tetrahydronaphthyl all of which may be either unsubstituted or substituted with one or more halogen, nitro, nitrile, alkyl, alklthio, methylenedioxy, amino, alkylamino, dialkylamino, alkoxycarbonylamino, dialkylamino-alkyleneimino, alkylcarbonylamino, formylamino or dicyanoethylidene groups in any combination; or R² is:

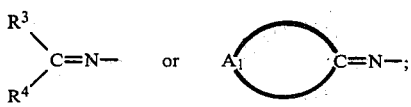

R³ is hydrogen, alkyl, alkylthio or cyano;
R⁴ is alkyl, thioalkyl, alkylthioalkyl, alkoxy, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl groups or $R^4$ is phenyl, aminocarbonyl, alkylaminocarbonyl, dialkylaminocarbonyl or an $R^5$CONH— or $R^5$CON (alkyl)— group where $R^5$ is hydrogen, alkyl or alkoxy; and $A_1$ is a divalent aliphatic chain, completing a five or six member ring, which includes one or two divalent oxygen, sulfur, sulfinyl or sulfonyl groups and which may also include one divalent amino, alkylamino or carbonyl group; in any combination; provided that the total number of aliphatic carbon atoms in $R^3$, $R^4$ and $A_1$, individually, may not exceed eight.

One equivalent of an oxime or hydroxyl reactant ($R^1OH$ or $R^2OH$) is reacted with the bis-carbamoyl halide in the presence of one equivalent of an acid acceptor, preferably in an inert solvent to produce the intermediate carbamate-sulfenyl-carbamoyl halide compound of this invention which is then reacted with the second oxime or hydroxyl reactant, ($R^1OH$ if $R^2OH$ was used in the first step; $R^2OH$ if $R^1OH$ was used first) in the presence of an acid acceptor to yield the desired unsymmetrical bis-carbamate compound. The acid acceptor employed can be either an organic or inorganic base such as triethylamine or sodium or potassium hydroxide. A phase transfer agent such as a crown ether may also be employed. Any conventional inert solvent can be used, such as benezene, toluene, dioxane, tetrahydrofuran, ethyl ether, methylene chloride or the like.

This reaction may also be carried out in two phase systems such as an aqueous solution of an inorganic base as one phase and an aromatic solvent including a quaternary ammonium salt as a phase transfer agent as the second phase. The reaction temperature is not critical. The reaction goes essentially to completion at room temperature. Elevated temperatures may be employed if it is desired to reduce the reaction time.

The hydroxyl and oxime reactants employed in the synthesis described above are known compounds which can be prepared by conventional methods. See for example U.S. Pat. Nos. 3,752,841; 3,726,908, 3,843,669 and Belgian Pat. Nos. 813,206 and 815,513.

The bis-carbamoyl fluoride starting reactants are prepared by reacting hydrogen fluoride with an appropriately substituted alkylisocyanate compound to form an alkylaminocarbonylfluoride compound which may then be reacted with sulfur dichloride to produce the desired bis-carbamoyl fluoride starting material.

The novel compounds of this invention can be prepared in a variety of ways. One method of preparing certain of the compounds of this invention is by the process shown in the following general reaction scheme:

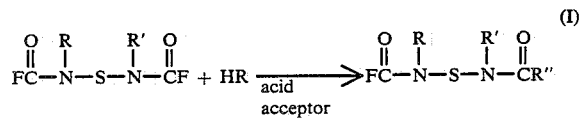

In the above general reaction scheme and those which are described below, R, R' and R" are as defined above.

Another reaction which may be employed for the preparation of compounds according to this invention is shown by the following general reaction scheme:

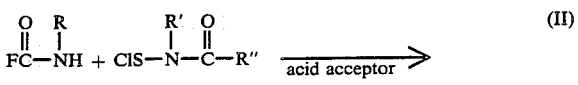

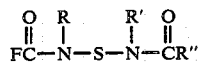

Procedure I is used for preparing compounds in which R" is bound to the carbonyl group through a divalent oxygen group while procedure II is preferred for producing compounds in which R" is bound to the carbonyl group by a carbon atom and may also be used to prepare compounds in which R" is bound to the carbonyl group through oxygen.

These reactions are conducted in the presence of at least one equivalent of an acid acceptor which may be either an organic or inorganic base such as triethylamine, tetraethylenediamine, pyridine or sodium or potassium hydroxide.

These reactions are also normally conducted in the presence of an inert solvent such as an ether, chlorinated hydrocarbon or aromatic solvent or any of the many inert organic solvents commonly used for such reactions. Illustrative of the inert solvents which may be used are methylene chloride, chloroform, dioxane, tetrahydrofuran, benzene, toluene, acetone, dimethoxyethane, dimethylformamide, acetonitrile and the like.

Reaction temperatures are not critical in the conduct of these reactions and may range from about $-50°$ C. to about $100°$ C. These reactions are preferably conducted at a temperature ranging from about $0°$ C. to about $40°$ C.

The bis-carbamoyl fluoride compounds employed as the starting materials in procedure I can be prepared conveniently by reacting hydrogen fluoride and an alkylisocyanate to form N-alkylcarbamoyl fluoride which may then be reacted with sulfur dichloride in the presence of an acid acceptor to produce the desired bis-carbamoyl fluoride compound. (See Example III).

The oxime compounds and chlorosulfenyl compounds employed as starting materials in the procedures described above are known compounds which can be prepared by conventional means. See for example U.S. Pat. Nos. 3,752,841, 3,726,908, 3,843,669, 3,843,689 and Belgian Pat. Nos. 813,206 and 815,513.

The following representative examples are presented to more clearly illustrate the preparation of the novel compounds of this invention:

EXAMPLE I

Preparation of N-Methyl-N-(N'-methyl-N'-formylaminosulfenyl)carbamoyl fluoride

To a solution of 9.0 g hydrogen fluoride in 100 ml toluene cooled to $-50°$ C. was added 25.6 g methyl isocyanate. After stirring for 45 minutes and allowing the mixture to warm to $-10°$ C., 56.4 g of N-methyl-N-formylaminosulfenyl chloride dissolved in 300 ml toluene was added. Triethylamine 45.4 g was added dropwise over a period of 0.5 hr while the temperature was maintained between $0°$ to $8°$ C. by external cooling. After stirring for 0.5 hr at ambient temperature, the reaction mixture was diluted with 200 ml ice water. The organic layer was separated, washed with water, dried and concentrated. Distillation of the residue yielded 22.4 g of product. b.p. $60°-62°$ C./0.2 mm.

Calcd. for $C_4H_7FN_2O_2S$: C, 28.91; H, 4.24; N, 16.86. Found: C, 29.01; H, 4.43; N, 16.26.

EXAMPLE II

Preparation of N-Methyl-N-(N'-methyl-N'-acetylaminosulfenyl)carbamoyl fluoride To a solution of 13.32 g hydrogen fluoride in 100 ml toluene, cooled to −50° C., was added 38.05 g of methyl isocyanate. The reaction mixture was allowed to warm to approximately 8° C. and stirred at that temperature for 1.5 hr. Then 93.0 g of N-methylacetylaminosulfenyl chloride dissolved in 250 ml toluene was added followed by dropwise addition of 67.4 g of triethylamine. The temperature was maintained at 0°–5° C. during the addition. After stirring at ambient temperature for 0.5 hr, the reaction mixture was diluted with 200 ml water. The toluene extract was further washed with water, dried with magnesium sulfate and evaporated in vacuo. Distillation of the residue yielded 40.0 g of product; b.p. 70°–74° C./0.5 mm.

Calcd. for $C_5H_9FN_2O_2S$: C, 33.32; H, 5.03; N, 15.55. Found: C, 32.71; H, 5.02; N, 15.13.

EXAMPLE III

Preparation of Bis-(N-Methyl-N-fluorocarbonylamino)sulfide

To a polypropylene reactor containing 80 g (4.0 m) of hydrogen fluoride in 1800 ml of toluene, cooled to −40° C. was added dropwise with stirring 228 g (4.0 m) of methylisocyanate, over a period of 20 min. The reaction mixture was allowed to warm to 0° C. and was maintained at this temperature for 1 hr. Then 206 g of freshly distilled sulfur dichloride was added followed by a slow addition of 346 g (4.4 m) of pyridine at −20° to −0° C. After stirring for 2 hrs. at −10° C. and for 16 hrs. at ambient temperature, the reaction mixture was diluted with 500 ml of water. The toluene layer was further washed with (3×500 ml) water dried and distilled to yield 244 g (66 percent) of the product. B.P. 55°–57° C./0.25 mm. m.p. 40°–41° C.

Calc'd for $C_4H_6F_2N_2O_2S$: C, 26.09; H, 3.28; N, 15.21 Found: C, 26.19; H, 3.20; N, 14–79.

EXAMPLE IV

Preparation of 1-Methylthioacetaldehyde O-[N-methyl-N-(N'-methyl-N'-fluoroformylaminosulfenyl)carbamoyl]oxime To a solution of 0.714 g 1-methylthioacetaldoxime and 1.36 g of bis-(N-methyl-N-fluorocarbonylamino)sulfide in 15 ml dioxane was added dropwise 0.687 g of triethylamine. After the solution was allowed to stand for 20 hrs, it was diluted with water and extracted with ethyl acetate. The organic extract was washed with water, dried with magnesium sulfate and concentrated under vacuum to yield 1.0 g of solid which was crystallized from isopropyl ether-ethyl acetate. m.p. 102°–104° C.

Calcd. for $C_7H_{12}FN_3O_3S_2$: C, 31.22; H, 4.49; N, 15.60. Found: C, 31.67; H, 4.69; N, 15.34.

EXAMPLE V

Preparation of 2-Methyl-2-methylthiopropionaldehyde O-[N-methyl-N-(N'-methyl-N'-fluoroformylaminosulfenyl)carbamoyl]oxime To a solution of 8.63 g bis-(N-methyl-N-fluorocarbonylamino)sulfide and 6.66 g of 2-methyl-2-methylthiopropionaldoxime in 40 ml dioxane and 40 ml toluene was added dropwise at 0°–5° C., 5.06 g of triethylamine over a period of 1 hr. The reaction mixture was allowed to stand overnight, diluted with water, and extracted in ethyl acetate. The organic extract was washed with water, dried and concentrated under reduced pressure. The residual oil crystallized on standing; weight of product 2.8 g, m.p. 70°–71° C.

Calcd. for $C_9H_{10}FN_3O_3S_2$: C, 36.35; H, 5.42; N, 14.13. Found: C, 36.60; H, 5.57; N, 13.39.

EXAMPLE VI

Preparation of 2,3-Dihydro-2,2-dimethyl-7-[N-methyl-N-(N'-methyl-N'-fluorocarbonylaminosulfenyl)carbamoyloxy]benzofuran To a solution of 5.0 g bis-(N-methyl-N-fluorocarbonylamino)sulfide and 5.0 g of 2,2-dimethyl-2,3-dihydrobenzofuran-7-ol in 75 ml dioxane was added 4.0 g of triethylamine. After allowing the reaction mixture to stand at ambient temperature for 6 days, it was diluted with 200 ml water and extracted in ethyl acetate. The ethyl acetate extract was washed with water, dried and concentrated under vacuo. Purification by silica gel chromatography yielded 5.0 g of product as a viscous oil.

Calcd. for $C_{14}H_{17}FN_2O_4S$: C, 51.21; H, 5.21; N, 8.53. Found: C, 51.90; H, 5.34; N, 8.60.

EXAMPLE VII

Preparation of 2-[O-[N-Methyl-N-(N'-methyl-N'-fluoroformylaminosulfenyl)carbamoyl]oximino]-3,5,5-trimethylthiazolidin-4-one To a suspension of 8.63 g bis-(N-methyl-N-fluorocarbonylamino)sulfide and 8.71 g of 3,5,5-trimethyl-2-oximinothiazolidin-4-one in 50 ml toluene was added dropwise 5.06 g of triethylamine. The temperature of the reaction solution was maintained between 0° to 5° C. After the addition of triethylamine all of the material was in solution. After stirring for an additional 2 hrs, the reaction product was isolated by the usual work-up. Concentration of the ethyl acetate solution yielded 1.5 g of the less soluble bis-carbamate. Crystallization of the mother liquor from isopropyl ether-hexane yielded 8.0 g of product. m.p. 111°–115° C.

Calcd. for $C_{10}H_{15}FN_4O_4S_2$: C, 35.49; H, 4.47; N, 16.56. Found: C, 36.04; H, 4.99; N, 16.18.

EXAMPLE VIII

Preparation of 1-[N-methyl-N-(N'-methyl-N'-fluoroformylaminosulfenyl)carbamoyloxy]naphthalene To a solution of 4.32 g of α-naphthol in 25 ml of dioxane was added 6.0 g of bis-(N-methyl-N-fluorocarbonylamino)sulfide. To this solution was added dropwise with stirring 3.03 g of triethylamine diluted with 5.0 ml of dioxane. After stirring for 28 hrs. at room temperature the solution was concentrated under reduced pressure and taken in ethyl acetate, washed with water, dried over magnesium sulfate and concentrated to 7.22 of an oil. The product crystallized from isopropyl ether, m.p. 58°–60° C.

Calcd. for $C_{14}H_{13}FN_2O_3S_3$: C, 54.53; H, 4.25; N, 9.09. Found: C, 54.58; H, 4.32; N, 8.96.

EXAMPLE IX

Preparation of 2-[O-[N-methyl-N-(N'-methyl-N'-fluoroformylaminosulfenyl)carbamoyl]oximino]-1,4-dithiane To a suspension of 3.68 g of bis-(N-methyl-N-fluorocarbonylamino)sulfide and 2.98 g of 2-oximino-1,4-dithiane in 125 ml of toluene was added with stirring 2.02 g of triethylamine. After the addition of the amine all the material was in solution. The reaction mixture was stirred at room temperature for 20 hrs. The insoluble bis-carbamate (1.0 g) was removed by filtration. The filtrate was washed with water, dried over magnesium sulfate and concentrated to yield 3.6 g of crystalline product. It was recrystallized from isopropylalcohol, m.p. 124°–126° C.

Calcd. for $C_8H_{12}FN_3O_3S_3$: C, 30.66; H, 3.86; N, 13.41. Found: C, 30.71; H, 3.75; N, 13.17.

EXAMPLE X

Preparation of 4-tert-Butylphenyl-N-methyl-N-(N'-methyl-N'-fluoroformylaminosulfenyl)carbamate 4-tert-Butylphenyl-N-methyl-N-(N'-methyl-N'-fluoroformylaminosulfenyl)carbamate was prepared by the procedure of Example IX by reacting 34.99 of bis-(N-methyl-N-fluorocarbonylamino)sulfide with 30 g of 4-tert-butylphenol in 600 ml of toluene with 20.24 g of triethylamine as acid acceptor. Weight of the product 29.54 g, m.p. 69°–72° C.

Analysis:

IR(KBr): 5.6 (COF), 5.84 (CO)μ.

NMR(CDCl$_3$): δ1.31 (s), 9H, C(CH$_3$)$_3$; δ3.44 (d), J=1.0 Hz, 3H, CH$_3$N; δ3.49 (s), 3H, CH$_3$N; δ7.1 (d), $J_{AB}$=8.4 Hz; δ7.42 (d), $J_{BA}$=8.5 Hz,4H (aromatic).

EXAMPLE XI

Preparation of 3-Isopropylphenyl-N-methyl-N-(N'-methyl-N'-fluoroformylaminosulfenyl)carbamate 3-Isopropylphenyl-N-methyl-N-(N'-methyl-N'-fluoroformylaminosulfenyl)carbamate was prepared by the procedure of Example IX by reacting 51.56 g of bis-(N-methyl-N-fluorocarbonylamino)sulfide with 40 g of 3-isopropylphenol in 600 ml of toluene with 29.34 g of triethylamine as acid acceptor to yield 77 g of an oil.

Analysis:

IR(neat): 5.6 (COF), 5.8 (CO)μ.

NMR(CDCl$_3$): δ1.18 (d), J=7.0 Hz, 6H, CH(CH$_3$)$_2$; δ2.5–3.0 (m), J=7.0 Hz, 1H, CH; δ3.27 (d), J=1.0 Hz, 3H, NCH$_3$; δ3.32 (s), 3H, NCH$_3$; δ6.7–7.3 (m), 4H, aromatic.

EXAMPLE XII

Preparation of 3,4,5-trimethylphenyl-N-methyl-N-(N'-methyl-N'-fluoroformylaminosulfenyl)carbamate 3,4,5-Trimethylphenyl-N-methyl-N-(N'-methyl-N'-fluoroformylaminosulfenyl)carbamate was prepared by the procedure of Example IX by reacting 38.67 g of bis-(N-methyl-N-fluorocarbonylamino)sulfide with 30 g of 3,4,5-trimethylphenol in 600 ml of toluene with 22.26 g of triethylamine as acid acceptor to yield 58.7 g of an oil.

Analysis:

IR(neat): 5.6 (COF), 5.81 (CO)μ.

NMR(CDCl$_3$): δ2.0 (s), 3H, CH$_3$; δ2.13 (s), 6H, CH$_3$; δ3.27 (s), 3H, NCH$_3$; δ3.31 (s), 3H, NCH$_3$; δ6.63 (s), 2H, aromatic.

EXAMPLE XIII

Preparation of 4-Nonylphenyl-N-methyl-N-(N'-methyl-N'-fluoroformylaminosulfenyl)carbamate 4-Nonylphenyl-N-methyl-N-(N'-methyl-N'-fluoroformylaminosulfenyl)carbamate was prepared by the procedure of Example IX by reacting 11.01 g of p-nonylphenol with 9.21 g of bis-(N-methyl-N-fluorocarbonylamino)sulfide in 250 ml of toluene with 5.06 g of triethylamine as acid acceptor to yield 16 g of an oil Analysis:

IR(neat): 5.58 (COF), 5.77 (CO)μ.

NMR(CDCl$_3$): δ1.5–2.0 (m), 19H, (C$_9$H$_{19}$); δ3.52 (s), 6H, —NCH$_3$; δ7.0–7.5 (m), 4H, aromatic.

EXAMPLE XIV

Preparation of 3-Dimethylaminophenyl-N-methyl-N-(N'-methyl-N'-fluoroformylaminosulfenyl)carbamate 3-Dimethylaminophenyl-N-methyl-N-(N'-methyl-N'-fluoroformylaminosulfenyl)carbamate was prepared by the procedure of Example IX by reacting 6.72 g of bis-(N-methyl-N-fluorocarbonylamino)sulfide with 5 g of 3-dimethylaminophenol in 100 ml of toluene with 3.69 g of triethylamine as acid acceptor to yield 10.43 g of an oil.

Analysis:

IR(neat): 5.6 (COF), 5.8 (CO)μ.

NMR(CDCl$_3$): δ2.86 (s), 6H, N(CH$_3$)$_2$; δ3.40 (s), 3H, NCH$_3$; δ3.43 (s), 3H, NCH$_3$; δ6.3–7.3 (m), 4H, aromatic.

EXAMPLE XV

Preparation of N-Methyl-N-(N'-methyl-N'-fluoroformylaminosulfenyl)propynylcarbamate N-Methyl-N-(N'-methyl-N'-fluoroformylaminosulfenyl)propynylcarbamate was prepared by the procedure of Example IX by reacting 33.15 g of bis-(N-methyl-N-fluorocarbonylamno)sulfide with 10 g of propargyl alcohol in 100 ml of toluene with 18.2 g of triethylamine as acid acceptor to yield 30 g of an oil.

Analysis:

IR(neat): 4.7 (C≡C); 5.58 (COF), 5.8 (CO)μ.

NMR(CDCl$_3$): 2.63 (t), J=2.5 Hz, 1H, C≡C—H; 3.41 (d), J∼1.0 Hz, 3H, N—CH$_3$; 3.43 l (s), 3H, NCH$_3$; 4.82 (d), J=2.5 Hz, 2H, CH$_2$.

EXAMPLE XVI

Preparation of 2-Isopropoxyphenyl-N-methyl-N-(N'-methyl-N'-fluoroformylaminosulfenyl)carbamate 2-Isopropoxyphenyl-N-methyl-N-(N'-methyl-N'-fluoroformylaminosulfenyl)carbamate was prepared by the procedure of Example IX by reacting 46.04 g of bis-(N-methyl-N-fluorocarbonylamino)sulfide with 40 g of 2-isopropoxyphenol in 750 ml of toluene with 25.29 g of triethylamine as acid acceptor to yield 73.64 g of an oil.

Analysis:

Calc'd for $C_{13}H_{17}FN_2O_4S$: C, 49.35; H, 5.42; N, 8.86. Found: C, 51.07; H, 5.57; N, 8.38.

IR(neat): 5.6 (COF), 5.78 (CO)μ.

EXAMPLE XVII

Preparation of 5,6,7,8-Tetrahydronaphthyl-N-methyl-N-(N'-methyl-N'-fluoroformylaminosulfenyl)carbamate 5,6,7,8-Tetrahydronaphthyl-N-methyl-N-(N'-methyl-N'-fluoroformylaminosulfenyl)carbamate was prepared by the procedure of Example IX by reacting 9.21 g of bis-(N-methyl-N-fluorocarbonylamino)sulfide with 7.41 g of 5,6,7,8-tetrahydro-1-naphthol in 300 ml of toluene with 5.05 g of triethylamine as acid acceptor to yield 9.5 g of an oil.

Analysis:
IR(neat): 5.6 (COF), 5.8 (CO)μ.
NMR(CDCl$_3$): δ1.6–1.9, (m), 4H; δ2.4–2.9, (m), 4H; δ3.44, (s) 3H, NCH$_3$; δ3.50, (s) 3H, NCH$_3$; δ6.8–7.2, (m), 3H, aromatic.

EXAMPLE XVIII

Preparation of 2-Propynyloxyphenyl-N-methyl-N-(N'-methyl-N'-fluoroformylaminosulfenyl)carbamate 2-Propynyloxyphenyl-N-methyl-N-(N'-methyl-N'-fluoroformylaminosulfenyl)carbamate was prepared by the procedure of Example IX by reacting 10.12 g of bis-(N-methyl-N-fluorocarbonylamino)sulfide with 8.1 g of 2-propargyloxyphenol in 200 ml of toluene with 5.3 g of triethylamine as acid acceptor. Weight of the product was 6.9 g, m.p. 80°–82° C.

Analysis: Calc'd for C$_{13}$H$_{13}$FN$_2$O$_4$S: C, 49.99; H, 4.19; N, 8.97. Found: C, 50.08; H, 4.21; N, 8.82.

EXAMPLE XIX

Preparation of 3-Phenoxyphenyl-N-methyl-N-(N'-methyl-N'-fluoroformylaminosulfenyl)carbamate 3-Phenoxyphenyl-N-methyl-N-(N'-methyl-N'-fluoroformylaminosulfenyl)carbamate was prepared by the procedure of Example IX by reacting 2.58 g of bis-(N-methyl-N-fluorocarbonylamino)sulfide with 2.68 g of 3-phenoxyphenol in 75 ml of toluene with 1.42 g of triethylamine as acid acceptor to yield 3.4 g of an oil.

Analysis: IR(neat): 5.63 (COF), 5.82 (CO)μ.
NMR(CDCl$_3$): δ3.4 (d), J=1.0 Hz, 3H, NCH$_3$; δ3.44 (s), 3H, NCH$_3$; δ6.8–7.5 (m), 9H, aromatic.

Illustrative of other new compounds which can be prepared by the processes described above are the following:

N-Methyl-N-(N'-propyl-N'-formylaminosulfenyl)carbamoyl fluoride.
N-Methyl-N-(N'-butyl-N'-acetylaminosulfenyl)carbamoyl fluoride.
2,3-Dihydro-2-methyl-7-[N-methyl-N-(N'-methyl-N'-fluoroformylaminosulfenyl)carbamoyloxy]benzofuran.
1-[N-Methyl-N-(N'-methyl-N'-fluoroformylaminosulfenyl)carbamoyloxy]5,6,7,8-tetrahydronaphthalene.
2-Methyl-2-methylsulfonyl propionaldehyde O-[N-methyl-N-(N'-fluoroformylaminosulfenyl)carbamoyl]oxime.
1-Isopropylthioacetaldehyde O-[N-methyl-N-(N'-methyl-N'-fluoroformylaminosulfenyl)carbamoyl]oxime.
2-Methyl-2-methoxypropionaldehyde O-[N-methyl-N-(N'-methyl-N'-fluoroformylaminosulfenyl)carbamoyl]oxime.
1-(2-Cyanoethylthio)acetaldehyde O-[N-methyl-N-(N'-methyl-N'-fluoroformylaminosulfenyl)carbamoyl]oxime.
2-Methyl-2-cyanopropionaldehyde O-[N-methyl-N-(N'-methyl-N'-fluoroformylaminousulfenyl)carbamoyl]oxime.
1-Methylthio-1-dimethylcarbamoylformaldehyde O-[N-methyl-N-(N'-methyl-N'-fluoroformylaminosulfenyl)cabamoyl]oxime.
2-[[O-[N-methyl-N-(N'-methyl-N'-fluoroformylaminosulfenyl)carbamoyl]oximino]]-4-methyl-tetrahydro-1,4-thiazin-3-one.
1-Methylthio-3,3-dimethylbutanone-2 O-[N-methyl-N-(N'-methyl-N'-fluoroformylaminosulfenyl)carbamoyl]oxime.
2-[[O-[N-methyl-N-(N'-methyl-N'-fluoroformylaminosulfenyl)carbamoyl]oximino]]-1,3-dithiolane.
4-[[O-[N-methyl-N-(N'-methyl-N'-fluoroformylaminosulfenyl)carbamoyl]oximino]]-5,5-dimethyl-1,3-dithiolane.
4-[[O-[N-methyl-N-(N'-methyl-N'-fluoroformylaminousulfenyl)carbamoyl]oximino]]-5-methyl-1,3-oxathiolane.
2-[[O-[N-methyl-N-(N'-methyl-N'-methyl-N'-fluoroformylaminosulfenyl)carbamoyl]oximino]]-3,3-dimethyl-1,4-dithiane.
2-[[O-[N-methyl-N-(N'-methyl-N'-fluoroformylaminosulfenyl)carbamoyl]oximino]]-3-isopropylthiazolidin-4-one.
2-[[O-[N-methyl-N-(N'-methyl-N'-fluoroformylaminosulfenyl)carbamoyl]oximino]]-4,5,5-trimethylthiazolidin-3-one.
4-Dimethylamino-3,5-xylyl-N-methyl-N-(N'-methyl-N'-fluoroformylaminosulfenyl)carbamate.
4-Methoxycarbonylamino-3,5-xylyl-N-methyl-N-(N'-methyl-N'-fluoroformylaminosulfenyl)-carbamate.
2-Isopropoxy-phenyl-N-methyl-N-(N'-methyl-N'-fluoroformylaminosulfenyl)carbamate.
3-sec-Butyl-phenyl-N-methyl-N-(N'-methyl-N'-fluoroformylaminosulfenyl)carbamate.
3,4-Xylyl-N-methyl-N-(N'-methyl-N'-fluoroformylaminosulfenyl)carbamate.
3,4-Methylenedioxyphenyl-N-methyl-N-(N'-methyl-N'-fluoroformyl aminosulfenyl)carbamate.
4-Methylthio-3,5-xylyl-N-methyl-N-(N'-methyl-N'-fluoroformylaminosulfenyl)carbamate.
2-Dioxalanylphenyl-N-methyl-N-(N'-methyl-N'-fluoroformylaminosulfenyl)carbamate.
1-Methylthioacetaldehyde O-[N-butyl-N-(N'-methyl-N'-fluoroformylaminosulfenyl)carbamoyl]oxime.
2-Methyl-2-methylthiopropionaldehyde O-[N-methyl-N-(N'-isopropyl-N'-fluoroformylaminosulfenyl)carbamoyl]oxime.
2-Methyl-2-methoxypropionaldehyde O-[N-methyl-N-(N'-butyl-N'-fluoroformylaminosulfenyl)carbamoyl]oxime.
2,4-Dinitro-6-sec-butyl-phenyl-N-methyl-N-(N'-methyl-N'-fluoroformylaminosulfenyl)carbamate
2,6-di-tert-butyl-4-(2,2-dicyanoethylidene)phenyl-N-methyl-N-(N'-methyl-N'-fluoroformylaminosulfenyl)carbamate.
3-Isopropyl phenyl-N-methyl-N-(N'-methyl-N'-fluoroformylaminosulfenyl)carbamate.
4-Isopropyl phenyl-N-methyl-N-(N'-methyl-N'-fluoroformylaminosulfenyl)carbamate.

3,5-di-tert-butyl-4-[N-methyl-N-(N'-methyl-N'-methyl-N'-fluoroformylaminosulfenyl)carbamoyloxy]benzylidene malononitrile.

1-Cyano-2,2-dimethylpropionaldehyde O-[N-methyl-N-(N'-methyl-N'-fluoroformylaminosulfenyl)carbamoyl]oxime.

1-Methylsulfonyl-3,3-dimethylbutanone-2O-[N-methyl-N-(N'-methyl-N'-fluoroformylaminosulfenyl)carbamoyl]oxime.

3-Methylsulfonylbutanone-2 O-[N-methyl-N-(N'-methyl-N'-fluoroformylaminosulfenyl)carbamoyl]oxime.

N-Methyl-N-(N'-methyl-N'-dodecanoylaminosulfenyl)carbamoyl fluoride.

All of the compounds of this invention can be produced simply and in excellent yield by the processes described above by simply selecting the appropriate reactants to produce the compound desired.

Selected species of the new compounds were evaluated to determine their pesticidal activity against mites, nematodes and certain insects, including an aphid, caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

SOUTHERN ARMYWORM LEAF SPRAY TEST

Larvae of the southern armyworm (*Prodenia eridania*, (Cram.)),-reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

FLY BAIT TEST

Four to six day old adult house flies (*Musca domestica*, L.), reared according to the specifications of the Chemical Specialties Manufacturing Association (Blue Book, McNair-Dorland Co., N.Y. 1964; pages 243-244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

MITE FOLIAGE SPRAY TEST

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

NEMATOCIDE TEST

The test organism used was the infective migratory larvae of the root-knot nematode, *Meloidogyne incognita* var *arcita*, reared in the greenhouse on roots of cucumber plants. Infected plants were removed from the culture, and the roots are chopped very finely. A small amount of this inoculum was added to a point jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds was rated as follows:

A=excellent control
B=partial control
C=no control
Dashes indicate no test conducted.

TABLE I

| Example | Compound | Aphid | Mite | Southern Armyworm | Mexican Bean Beetle | Housefly | Nematode |
|---|---|---|---|---|---|---|---|
| II | N—Methyl-N—(N'—methyl-N'—acetyl aminosulfenyl)carbamoyl fluoride. | C | C | C | C | B | B |
| IV | 1-Methylthioacetaldehyde O—[N—methyl-N—(N'—methyl-N'—fluoroformylaminosulfenyl)carbamoyl]oxime. | A | A | A | A | A | A |
| V | 2-Methyl-2-methylthiopropionaldehyde O—[N—methyl-N—(N'—methyl-N' fluoroformylaminosulfenyl)carbamoyl]oxime. | A | A | A | A | A | — |
| VI | 2,3-Dihydro-2,2-dimethyl-7-[N—methyl-N—(N'—methyl-N'—fluorocarbonylaminosulfenyl)carbamoyloxy]benzofuran. | A | B | A | A | A | A |
| VII | 2-[O—[N—Methyl-N—(N'—methyl-N'—fluoroformylaminosulfenyl)carbamoyl]oximino]-3,5,5-trimethylthiazolidin-4-one | B | B | A | A | A | — |
| VIII | 1-[N—Methyl-N—(N'—methyl-N'—fluoroformylaminosulfenyl)carbamoyloxy]naphthalene. | A | C | A | A | C | — |
| IX | 2-[O—[N—Methyl-N—(N'—methyl-N'—fluoroformylaminosulfenyl)carbamoyl]oximino]-1,4-dithiane | A | A | A | A | A | — |

| Example | Compound | Aphid | 2-Spotted Mite | Southern Armyworm | Mexican Bean Beetle | Housefly | Nematode |
|---|---|---|---|---|---|---|---|
| XI | 3-Isopropylphenyl-N—methyl-N—(N'—fluoroformylaminosulfenyl)carbamate | A | C | A | A | A | — |
| XII | 3,4,5-Trimethylphenyl-N—methyl-N—(N'—methyl-N—fluoroformylaminosulfenyl)carbamate | A | C | A | A | A | C |
| XVI | 2-Isopropoxyphenyl-N—methyl-N—(N'—methyl-N'—fluoroformylaminosulfenyl)carbamate | A | C | C | A | A | A |
| XVII | 1-[N—methyl-N—(N'—methyl-N'—fluoroformyl- | A | C | A | A | A | A |

TABLE I-continued

| | | | | | | | |
|---|---|---|---|---|---|---|---|
| | aminosulfenyl)carbamoloxy]-5,6,7,8-tetrahydronaphthalene | | | | | | |
| XVIII | 2-Propynyloxyphenyl-N—methyl-N'—(N'—methyl-N'—fluoroformylaminosulfenyl)carbamate | A | A | A | A | A | A |

The pesticidally active compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a non-phytotoxic solvent such as acetone, xylene, or nitrobenzene and dispersing the toxicants in water with the aid of suitable surface active emulsifying and dispersing agents.

The choice of dispersing and emulsifying agents and the amount employed in dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 weight percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, mites and nematodes upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents or the spray schedule, and they may be used in the soil, upon the seeds, or the roots of plant without injuring either the seeds or roots of plants.

As indicated above the compounds of this invention are also useful as intermediates in the preparation of more complex pesticidally active compounds.

What is claimed is:

1. A compound of the formula:

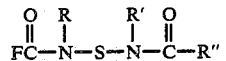

wherein:
R and R' are the same or different and are alkyl groups having from one to four carbon atoms;
R" is:
(a) hydrogen; or
(b) alkyl, cycloalkyl, phenyl, phenylalkyl, naphthyl, alkenyloxy, alkynyloxy, phenoxy, napthoxy, 5,6,7,8-tetrahydronaphthoxy, benzofuranoxy, benzothienoxy or methylenedioxyphenoxy, all of which may be unsubstituted or substituted with one or more chloro, bromo, fluoro, cyano, nitro, alkyl, alkynyloxy, phenoxy, phenyl, 2-dithiolanyl, 2-dioxalanyl, alkoxy, haloalkyl, dialkylamino, cyanoalkyl, dicyanoethylidine or alkylthio groups in any combination.

2. The compound of claim 1 wherein R" is (a) hydrogen or alkyl or (b) alkenyloxy, alkynyloxy, phenoxy, naphthoxy, 5,6,7,8-tetrahydronaphthoxy or benzofuranoxy all of which may be unsubstituted or substituted with one or more chloro, bromo, fluoro, cyano, nitro, alkyl, alkynyloxy, phenoxy, phenyl, 2-dithiolanyl, 2-dioxalanyl, alkoxy, haloalkyl, dialkylamino, cyanoalkyl, dicyanoethylidine or alkylthio groups in any combination.

3. The compound of claim 1 wherein R and R' are methyl and R" is (a) hydrogen or alkyl or (b) alkenyloxy, alkynyloxy, phenoxy, naphthoxy, 5,6,7,8-tetrahydronaphthoxy or benzofuranoxy all of which may be unsubstituted or substituted with one or more chloro, bromo, fluoro, cyano, nitro, alkyl, alkynyloxy, phenoxy, phenyl, 2-dithiolanyl, 2-dioxalanyl, alkoxy, haloalkyl, dialkylamino, cyanoalkyl, dicyanoethylidine or alkylthio groups in any combination.

4. The compound of claim 1 wherein R and R' are methyl and R" is substituted phenoxy wherein the permissible substituents are one or more alkyl or alkylthio groups in any combination.

5. The compound of claim 1 wherein R and R' are methyl and R" is substituted phenoxy wherein the permissible substituents are one or more alkyl or dialkylamino groups in any combination.

6. The compound of claim 1 wherein R" is benzofuranoxy, alkynyloxy, naphthoxy, 5,6,7,8-tetrahydronaphthoxy or either substituted or unsubstituted phenoxy wherein the permissible substituents are one or more alkyl, alkoxy, dialkylamino, alkynyloxy, or phenoxy substituents in any combination.

7. The compound of claim 1 wherein R and R' are methyl and R" is benzofuranoxy, alkynyloxy, naphthoxy, 5,6,7,8-tetrahydronaphthoxy or either substituted or unsubstituted phenoxy wherein the permissible substituents are one or more alkyl, alkoxy, dialkylamino, alkynyloxy, or phenoxy substituents in any combination.

8. The compound of claim 1 wherein R and R' are methyl.

9. The compound of claim 1 wherein R" is hydrogen.

10. The compound of claim 1 wherein R" is a substituted phenoxy.

11. The compound of claim 1 wherein R" is naphthoxy.

12. The compound of claim 1 wherein R" is 5,6,7,8-tetrahydronaphthoxy.

13. The compound of claim 1 wherein R" is benzofuranoxy.

14. The compound of claim 1 which is 1-[N-methyl-N-(N'-methyl-N'-fluoroformylaminosulfenyl)carbamoyloxy]naphthalene.

15. The compound of claim 1 which is 3,4,5-trimethylphenyl-N-methyl-N-(N'-methyl-N-fluoroformylaminosulfenyl)carbamate.

16. The compound of claim 1 which is 2-isopropoxyphenyl-N-methyl-N-(N'-methyl-N'-fluoroformylaminosulfenyl)carbamate.

17. The compound of claim 1 which is 1-[N-methyl-N-(N'-methyl-N'-fluoroformylaminosulfenyl)carbamoyloxy]-5,6,7,8-tetrahydronaphthalene.

18. 2,3-Dihydro-2,2-dimethyl-7-[N-methyl-N-(N'-methyl-N'-fluorocarbonylaminosulfenyl)carbamoyloxy]benzofuran.

* * * * *